(12) United States Patent
Tallavarjula et al.

(10) Patent No.: US 7,813,895 B2
(45) Date of Patent: Oct. 12, 2010

(54) METHODS FOR PLASMA MATCHING BETWEEN DIFFERENT CHAMBERS AND PLASMA STABILITY MONITORING AND CONTROL

(75) Inventors: Sairaju Tallavarjula, Santa Clara, CA (US); Aaron Hunter, Santa Cruz, CA (US); Joseph Ranish, San Jose, CA (US); Johanes Swenberg, Los Gatos, CA (US); Robert M. Haney, Mountain View, CA (US)

(73) Assignee: Applied Materials, Inc., Santa Clara, CA (US)

( * ) Notice: Subject to any disclaimer, the term of this patent is extended or adjusted under 35 U.S.C. 154(b) by 346 days.

(21) Appl. No.: 11/829,762

(22) Filed: Jul. 27, 2007

(65) Prior Publication Data

US 2009/0030632 A1 Jan. 29, 2009

(51) Int. Cl.
*G06F 11/30* (2006.01)
(52) U.S. Cl. .................... 702/182; 702/81; 439/9
(58) Field of Classification Search ............. 702/81–84; 438/9, 16, 710; 216/59–61; 356/72, 316
See application file for complete search history.

(56) References Cited

U.S. PATENT DOCUMENTS

| | | | |
|---|---|---|---|
| 4,312,732 A | 1/1982 | Degenkolb et al. | |
| 5,288,367 A | 2/1994 | Angell et al. | |
| 5,526,110 A * | 6/1996 | Braymen | 356/316 |
| 5,653,894 A | 8/1997 | Ibbotson et al. | |
| 5,658,423 A | 8/1997 | Angell et al. | |
| 5,711,843 A | 1/1998 | Jahns | |
| 5,835,230 A * | 11/1998 | McAndrew et al. | 356/437 |
| 5,885,472 A | 3/1999 | Miyazaki et al. | |
| 5,986,747 A | 11/1999 | Moran | |
| 6,153,115 A | 11/2000 | Le et al. | |
| 6,368,975 B1 * | 4/2002 | Balasubramhanya et al. | 438/706 |
| 6,381,008 B1 | 4/2002 | Branagh et al. | |
| 6,413,867 B1 | 7/2002 | Sarfaty | |
| 6,419,846 B1 | 7/2002 | Toprac et al. | |
| 6,455,437 B1 | 9/2002 | Davidow et al. | |
| 6,521,080 B2 | 2/2003 | Balasubramhanya et al. | |
| 6,864,109 B2 | 3/2005 | Chang et al. | |
| 6,896,763 B2 | 5/2005 | Balasubramhanya et al. | |
| 7,169,625 B2 * | 1/2007 | Davis et al. | 438/9 |
| 2003/0147770 A1 * | 8/2003 | Brown et al. | 422/24 |
| 2006/0164657 A1 * | 7/2006 | Chalmers et al. | 356/630 |

* cited by examiner

*Primary Examiner*—Manuel L Barbee
(74) *Attorney, Agent, or Firm*—Diehl Servilla, LLC (57) ABSTRACT

Methods for matching semiconductor plasma processing chambers using a calibrated spectrometer are disclosed. In one embodiment, plasma attributes are measured for a process in a reference chamber and a process in a sample chamber. Measuring the plasma attributes during process perturbations allows for the correlation of process parameters to the plasma optical emission spectra. The process parameters can then be adjusted to yield a processed substrate which matches that of the reference chamber. Methods for monitoring the stability of a plasma processing chamber using a calibrated spectrometer are also disclosed.

22 Claims, 6 Drawing Sheets

500 Plasma Matching Between Different Chambers

502 — Calibrate at least one spectrometer using at least one standardized light source

504 — Process a substrate in a reference plasma chamber, record the optical emission spectra using a calibrated spectrometer, and calculate the ratio of the intensities of the selected wavelengths against the total intensity.

506 — Process another substrate in a different plasma chamber using the same parameters, record the optical emission spectra during the processing using a calibrated spectrometer, and calculate the ratio of the intensities of the selected wavelengths against the total intensity.

508 — Measure the desired surface characteristics on both substrates.

510 — Compare the differences in the calculated intensity ratios for both chambers as a function of the surface characteristics.

512 — Vary the operating parameters, one at a time, and process a substrate. Collect OES data and surface characteristics data for each set of operating conditions.

514 — Using the sensitivities to each of the parameters, determine which operating parameters need to be optimized for chamber matching.

516 — Modify the parameters of the second chamber to get the same substrate surface characteristics as the reference chamber.

518 — Repeat steps 506 through 516 for additional processing chambers.

*FIG. 5*

600 Plasma Stability Monitoring and Control

602 — Calibrate at least one spectrometer using at least one standardized light source

604 — Process a substrate in a plasma chamber, record the optical emission spectra using a calibrated spectrometer, and calculate the ratio of the intensities of the selected wavelengths against the total intensity.

606 — Vary the operating parameters, one at a time, and process a substrate. Collect OES data and surface characteristic data for each set of operating conditions.

608 — Correlate the sensitivity of the surface characteristics to the modified parameter as a function of the OES data.

610 — Monitor the drift in plasma OES over time to predict when a substrate process will be outside of the allowable range.

*FIG. 6*

METHODS FOR PLASMA MATCHING BETWEEN DIFFERENT CHAMBERS AND PLASMA STABILITY MONITORING AND CONTROL

TECHNICAL FIELD

Embodiments of the present invention pertain to semiconductor substrate processing systems. More particularly, techniques for matching a substrate processing chamber with a reference substrate processing chamber are disclosed. Additionally, techniques to monitor the plasma stability of a process chamber over a period of time are disclosed.

BACKGROUND ART

Within the semiconductor industry, an ever present need exists for improved process repeatability and control. As new generations of integrated circuits employ smaller feature sizes than were contemplated in previous generations, greater demands are placed on the integrated circuit fabrication process. Deposition and etching of one or more layers on a semiconductor substrate in a plasma environment are two of the most common steps in integrated circuit manufacturing. In addition plasma assisted doping (by implantation of species or incorporation of species are being used extensively in the transistor fabrication. Considering that many discrete plasma processing chambers are employed in either the same manufacturing facility or different manufacturing facilities to manufacture products intended to have the same properties, it is very important that a consistent result is produced from one chamber to another chamber either in the same facility or a different facility. Therefore, to ensure that a consistent film is deposited or etched on the substrate, it is important to make sure that the various plasma processing chambers operate substantially in the same manner.

To ensure that a correct amount and quality of film is deposited, etched, implanted or incorporated, a production process chamber needs to be calibrated against a "reference" chamber (which may also be referred to as a "good" chamber or "golden" chamber). The procedure used to compare chambers is sometimes called chamber qualification. Chamber qualification procedures are used at various times during a chamber's use. When a process chamber is newly manufactured, the chamber must be qualified. The new chamber is typically matched to a "golden" chamber to ensure the new chamber will perform according to its specification. Once the chamber is qualified, the chamber can then be shipped to a semiconductor manufacturing facility. Once the chamber arrives at the semiconductor manufacturing facility, the chamber is reassembled and "qualified" again prior to processing the production materials. In addition, production chambers must undergo regular maintenance or cleaning. After maintenance or chamber cleaning, the chamber needs to be "qualified" again prior to running production wafers. Stringent chamber matching techniques that utilize comprehensive plasma monitoring are needed to ensure process repeatability and control in semiconductor manufacturing.

To ensure that a consistent substrate processing occurs in different chambers, each plasma processing chamber is typically matched to a reference "golden" chamber. The plasma state of the chamber during processing needs to match that of a selected process in a "reference" chamber to ensure the chamber and process are functioning as expected. If the plasma state of the process chamber does not match that of a selected "reference" chamber, the processing parameters can be modified to obtain a matching plasma state, resulting in equivalent products.

Besides chamber matching, monitoring a single chamber over a period of time will decrease chamber downtime. By monitoring the plasma state, the operator can predict when a process will result in product which is outside of the acceptable ranges. This will allow for the determination of when preventative maintenance must be performed on the plasma chamber prior to generating products which do not meet the acceptance criteria.

During a plasma process, certain plasma "attributes", such as the plasma's electromagnetic emissions, the RF power delivered to a wafer pedestal, wafer reflectance, process pressure and process temperature, manifest low frequency fluctuations that contain significant information about the plasma process and the plasma chamber. These attributes affect the resultant process, thereby giving different substrates different surface characteristics. The intensity of a plasma's optical emission spectra (OES) during plasma processing contains information related to the process state, process event and process chamber. OES states are affected to different degrees by varying chamber conditions and by process parameter changes.

While certain methods exist for monitoring process chambers and matching process chamber performance, there is a need for techniques to more accurately match substrate processing chambers to a reference substrate process chamber. There is also a need to more accurately monitor the short- and long-term stability of a plasma processing chamber.

SUMMARY

One or more embodiments of the invention pertain to methods for matching the plasma states of different processing chambers to a reference chamber. Additionally, embodiments of the invention also disclose methods for monitoring the stability, both short- and long-term, of a single plasma processing chamber. One or more embodiments of the invention use a standardized light source to calibrate at least one spectrometer. According to one or more embodiments, spectrometers calibrated to the same reference standard assure that the optical emission spectra from various processing chambers are compared to a uniform external standard.

In one embodiment, a method of matching the performance of process chambers, comprises calibrating at least a first spectrometer with at least a first standardized light source and collecting calibration data; collecting optical emission spectroscopy (OES) data using the at least first spectrometer during a first reference process utilizing a reference substrate, under known process parameters; collecting OES data using the at least first spectrometer during a second plasma process for a second substrate under process parameters substantially the same as the first process; measuring the degree of surface characteristic modification for the first and second substrates and correlating the degree of surface characteristic modification with the OES data for each substrate, wherein the correlation of OES data and surface characteristic modification of the second process is compared to the correlation of OES data and surface characteristic modification of the first process.

In another embodiment, the method may further comprise varying the process parameters of the second process, and processing a substrate using the varied parameters while collecting OES data; measuring the degree of surface characteristic modification of the substrate using varied parameters; correlating the degree of surface characteristic modification and the OES data obtained from the substrate using varied process to determine the OES data sensitivity to the varied process parameters; adjusting the process parameters of the second process based on the correlation data so that the surface characteristic modification of at least a third processed substrate would match the reference substrate. According to one embodiment, the first spectrometer is calibrated by measuring total intensity of light generated by the first standardized light source at selected wavelengths. In one or more embodiments, the first spectrometer is calibrated using a second standardized light source and measuring the intensity of light at selected wavelengths. According to certain embodiments, the second process is performed in the same chamber operated at a later time.

According to certain embodiments, the modified process parameter of the second process is selected from a group consisting of RF power, chamber pressure, reflected power, nitrogen flow rate, helium leak amount, wafer type, wafer temperature, base oxide amount, helium content of the nitrogen, oxygen content and moisture content. In one embodiment, the second standardized light source emits discrete wavelengths. In certain embodiments, the first standardized light source has a continuous spectral emission.

Another embodiment pertains to a method of monitoring the plasma stability of a processing chamber, comprising calibrating at least a first spectrometer with at least a first standardized light source and collecting calibration data; collecting optical emission spectroscopy (OES) data using the at least first spectrometer during a reference plasma process for a reference substrate in a processing chamber under known process parameters; collecting OES data using the at least first spectrometer during a second plasma process for a second substrate in the same processing chamber under process parameters substantially the same as the first process and comparing the OES data obtained during the second process to the calibration data; varying the processing parameters of the process, and processing a substrate under the varied parameters while collecting OES data; measuring the degree of modification of a surface characteristic of the processed substrates and correlating the degree of modification of a surface characteristic and the OES data to determine the sensitivity to the modified process parameters; and monitoring the OES data during processing on at least a second substrate to predict when the at least second substrate will have a surface characteristic outside of the acceptable range.

In one embodiment, only one spectrometer is employed. According to certain embodiments, the first spectrometer is calibrated by measuring total intensity of light generated by the first standardized light source at selected wavelengths. In one or more embodiments, the first spectrometer is calibrated using a second standardized light source and measuring the intensity of light at selected wavelengths. In certain embodiments, the standardized light source comprises a plurality or bundle of light emitting diodes. According to one or more embodiments, the process is selected from a group consisting of decoupled plasma nitridation, decoupled plasma oxidation, atomic layer deposition (ALD), plasma immersion ion implantation (P3i), plasma enhanced ALD (PE ALD), and remote plasma oxidation (RPO).

Embodiments of the invention provide methods of calibrating a spectrometer, which is then used to match the resultant substrate from a processing chamber based on the plasma optical emission spectra (OES). In one embodiment, a method includes calibrating a spectrometer, or detector, over a multitude of electromagnetic frequencies, collecting OES reference data for a first substrate processing operation in a reference chamber operating under best known conditions under known process parameters, comparing the OES data from the reference processing operation to the reference data, processing a second substrate in a different plasma processing chamber while collecting OES data from the second chamber and comparing the OES data from the second processing to the reference data from the reference processing chamber. The surface characteristics (e.g., degree of nitrogen dosing) of both substrates is determined by a suitable analytical technique, such as x-ray photoelectron spectroscopy (XPS). The desired surface characteristic can be correlated to the OES data. The processing conditions of the second chamber are modified, on an individual basis, and a substrate is processed while collecting OES data. The surface characteristics are determined, and a correlation to the plasma OES can be determined. From the obtained data, the sensitivity of the OES to various operating parameters can be determined. This will allow for matching the plasma OES from the second chamber to the reference chamber by modifying the operating parameters as needed.

In another embodiment of the invention, the plasma OES is monitored to maintain peak operating efficiency of the chamber. Trends in the OES data will predict when a processing chamber will generate a product which does not meet the acceptable dosing levels.

BRIEF DESCRIPTION OF THE DRAWINGS

So that the manner in which the features of various embodiments of the invention described herein are attained and can be understood in detail, a more particular description of embodiments of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Embodiments of the disclosed invention involve calibrating a spectrometer with at least a primary standard light source, measuring the optical emission spectrum (OES) of a plasma process in a reference processing chamber and the OES of a plasma process in a second processing chamber. According to one or more embodiments, by correlating the plasma emissions with a desired surface characteristic (e.g., nitrogen dose or N-dose during plasma nitridation), the processing parameters of the second chamber are adjusted so the resultant product of the second chamber matches that of the reference chamber. Other embodiments of the disclosed invention involve calibrating a spectrometer with at least a primary standard light source, measuring the OES of a plasma process in which the resultant substrate made by the plasma process has desired characteristics, and continually monitoring the plasma OES for signal drift which would indicate the production of end products not having desired characteristics. While embodiments of the present invention are described herein primarily with reference to nitrogen-based plasma processes (e.g., decoupled plasma nitridation), it will be understood that the principles described herein can be used for any type of plasma process. Non-limiting examples of other types of plasma processes include DPO (Decoupled Plasma Nitridation), RPO (Remote Plasma Oxidation) and plasma pre-cleaning processes.

It will be appreciated that use of a standard stable external light source to calibrate a spectrometer virtually eliminates any variability in measurement due to spectrometer drifts (or drifts associated with fiber optics/electronics used to collect data). According to embodiments of the invention, one or more process parameters (e.g., RF power) are used to make each process chamber read the same value or to within some defined limits for a given best known method recipe set of conditions. Thereafter, each process chamber can be monitored over time to detect any drifts in process conditions that affect properties of the substrates processed in the chambers. Drifts can be caused by changes in any of the parameters described above. But the common ones are leak - and hence oxygen/moisture mixing with nitrogen. In the case of oxygen, or for any other species of interest, the peak emission wavelength of laser diodes and LEDS can be adjusted by changing the diode materials. Large differences in peak wavelengths are achieved by using different semiconductor systems, such as GaAlAs—GaAs for red & IR versus SiC—GaN for blue. Minor variations in peak wavelength can be achieved by adjustments in the doping levels. So diodes can be made having peak emission wavelengths corresponding to that of the oxygen emission line at 844.6 nm. With an accurate power supply, these diodes can be used to calibrate optical sensors.

In addition, helium leaks in the chamber during chucking can cause drifts. An allowable drift can be defined, after which N-dose changes will be seen. Typically, small changes do not cause sufficient drift in N-dose. According to embodiments of the invention, a process is provided in which high sensitivity to drift is provided, and the process will detect drift in plasma emission before the N-dose results measured by XPS showing drift. Accordingly, the process chamber can be proactively monitored rather than waiting for the process chamber to drift out of a controlled process state as determined by daily monitoring by end users of the process chamber.

Details of how plasma emission spectrum data can be collected and how principal component analysis can be used to identify principal components have been disclosed in commonly assigned U.S. Pat. No. 6,455,437, entitled "Method and Apparatus For Monitoring The Process State of A Semiconductor Device Fabrication Process, issued on Sep. 24, 2002, U.S. Pat. No. 6,413,867, entitled "Film Thickness Control Using Spectral Interferometry", issued on Jul. 2, 2002, U.S. Pat. No. 6,368,975, entitled "Method and Apparatus For Monitoring A Process By Employing Principal Component Analysis", issued on Apr. 9, 2002, and U.S. Pat. No. 7,169,625, entitled "Method for Automatic Determination of Semiconductor Plasma Chamber Matching and Source of Fault By Comprehensive Plasma Monitoring", issued on Jan. 30, 2007. All of the aforementioned patents are incorporated herein by reference in their entireties. According to one or more embodiments of the present invention, plasma chambers can be calibrated to an absolute standard. In these embodiments, a calibrated light source, having a reference absolute intensity, is employed to standardize one or more spectrometers. These standardized spectrometers can be utilized in different plasma chambers in different locations to match the plasma processes performed in the chambers. Utilizing such chamber matching, desirably, the resultant products produced in the different chambers conform to a predetermined and acceptable product standard. In other embodiments, a second light source is utilized to calibrate one or more spectrometers by determining the total intensity or area under the curve for a light source at one more predetermined wavelengths.

Figure 1:
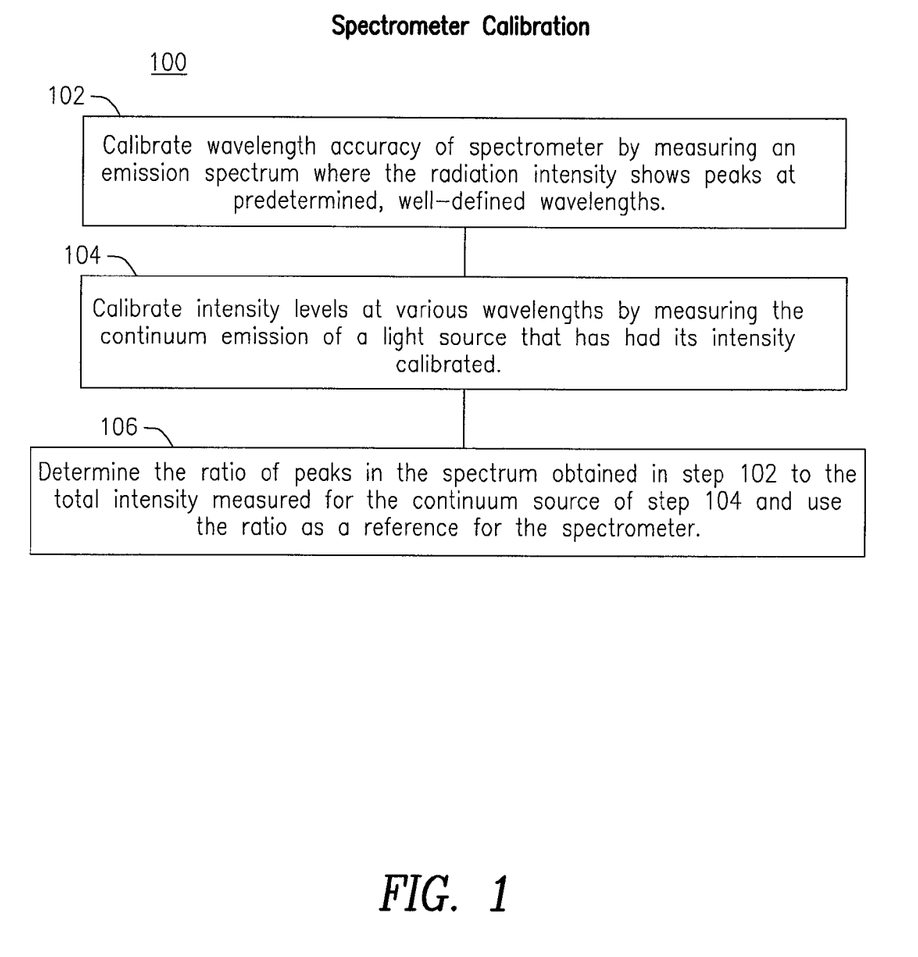
FIG. 1 is a flowchart illustrating the steps of a method for calibrating a spectrometer with primary standard light sources.
Figure 3:
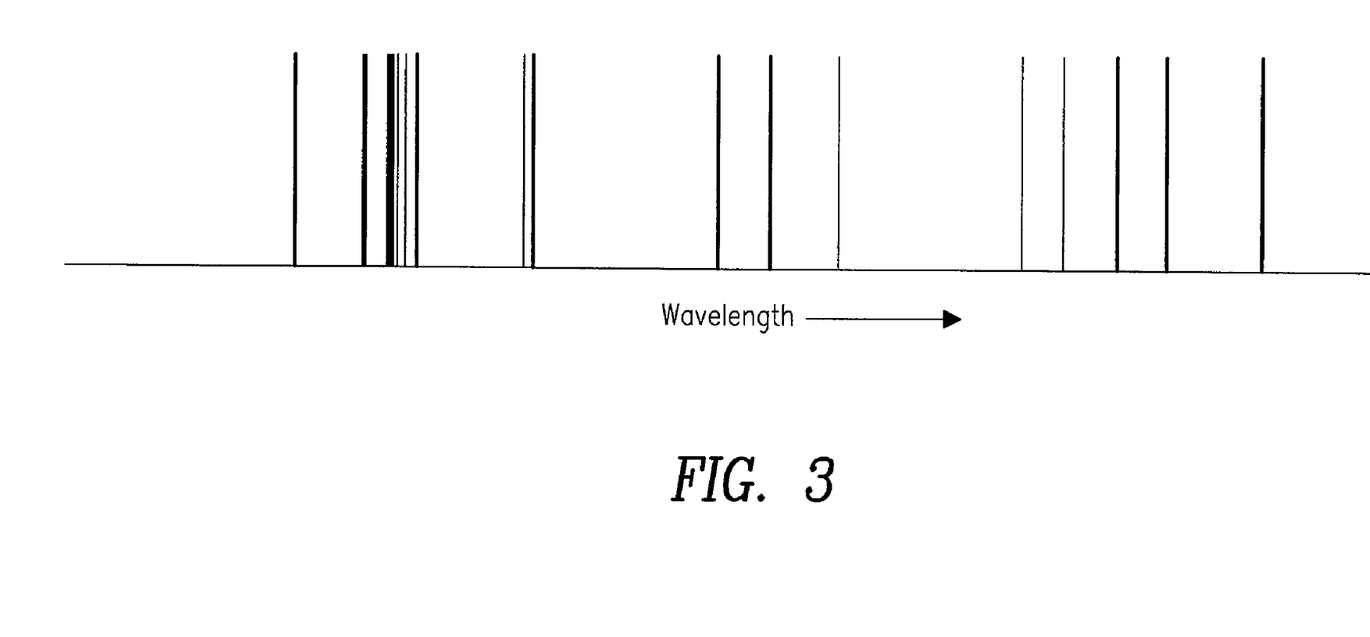
FIG. 3 shows graphical output for known wavelengths of oxygen atomic emission.

One embodiment of a process 100 is depicted in FIG. 1 as a flowchart of steps to calibrate a spectrometer using at least one standard light source. In step 102, the wavelength accuracy of a spectrometer is calibrated by measuring an emission spectrum where the radiation intensity shows peaks at well defined wavelengths from a known light source. This can be accomplished with light sources such as, but not limited to, hollow-cathode lamps, laser diodes and light emitting diodes. An example of the spectral fingerprinting used in this step can be seen in FIG. 3, which shows the discrete spectral lines from the atomic emission spectrum for the oxygen atom. (Oxygen spectra can vary depending on the excitation method and source, this is an example)

Figure 2:
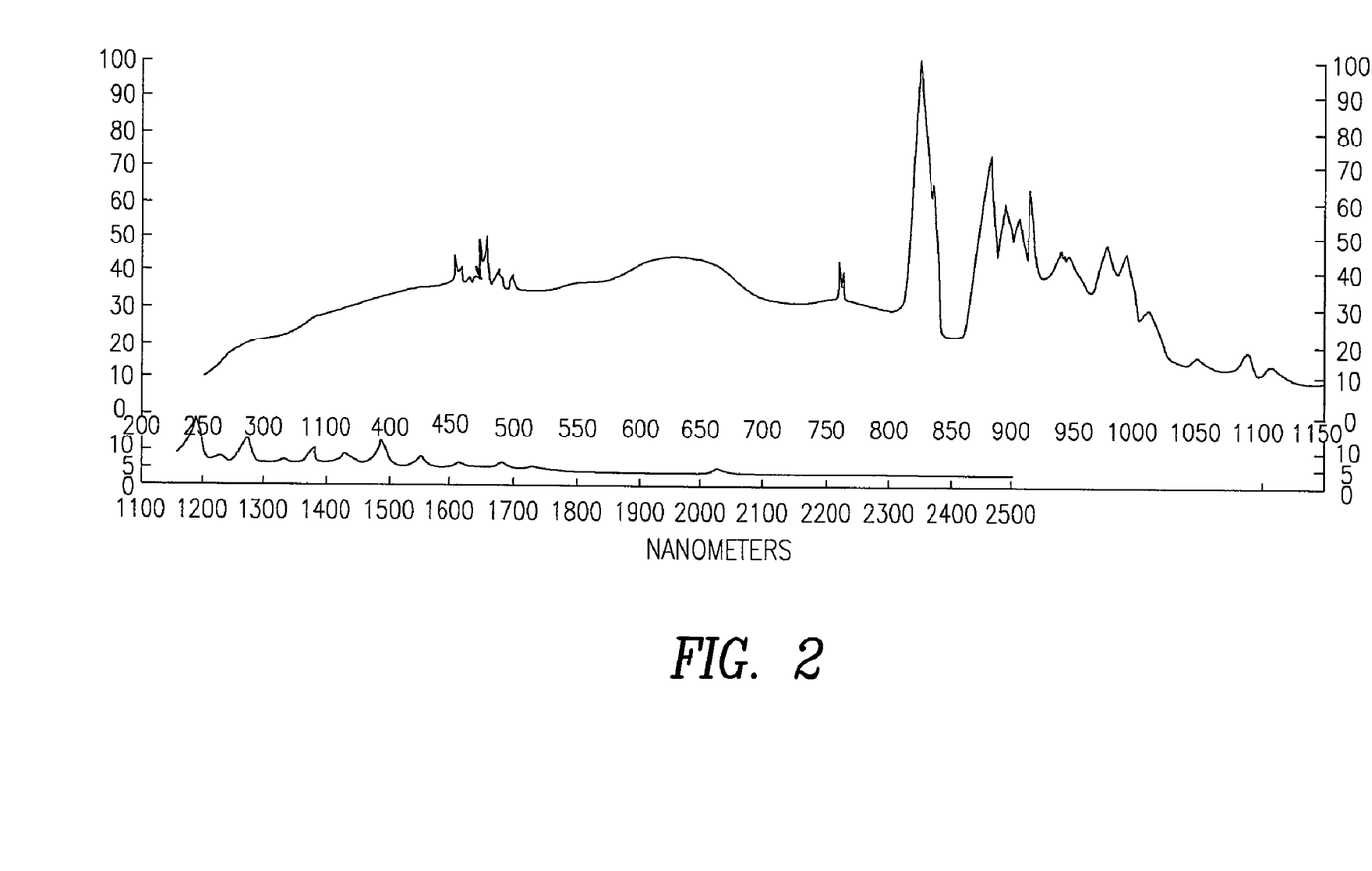
FIG. 2 shows representative electromagnetic spectrum emitted from a spectrum from a known light source, a Xenon arc lamp.

Once the spectral position of the wavelengths has been calibrated, the intensity levels at a selected range of wavelengths can be calibrated as shown in step 104 by measuring the continuum emission of a light source that has had its intensity calibrated. See FIG. 2 for an example spectrum from a continuum source, which shows the spectrum of a Xenon arc lamp. In one or more embodiments, an incandescent lamp or deuterium lamp, which has had its intensity calibrated against a primary standard black body furnace, available from the National Institute of Standards and Technology (NIST) and other sources can be used. In another embodiment, a calibrated continuum source can be used to calibrate the detector response with wavelength filters employed, thus combining steps 102 and 104 into one measurement. It should be noted that steps 102 and 104 can be performed in interchangeable order, and the number designation associated with each step is illustrative of only one embodiment of the invention. In step 106, the ratio of the peaks obtained from step 102 to the total intensity measured for the continuum source of step 104 is determined. This ratio will be used as a reference for the spectrometer. The spectrometer can be calibrated with the standardized light sources outside of the plasma processing chamber. Alternatively, the standardized light sources can be located within the plasma processing chamber. The standard light source emission would be measured by the spectrometer through a viewport in the plasma processing chamber.

Figure 4:
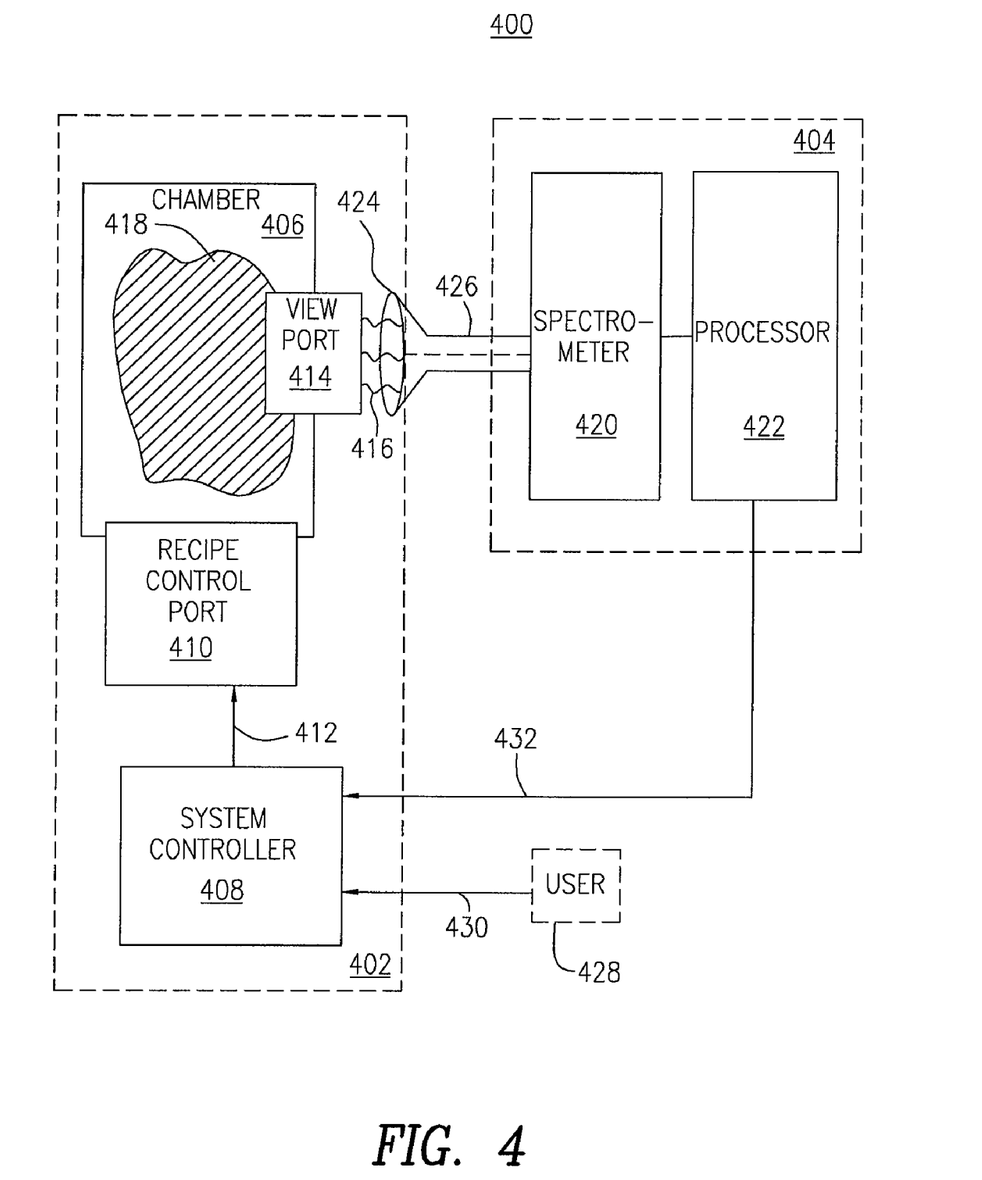
FIG. 4 is a block diagram of a processing system comprising a plasma system and a process monitoring system.

FIG. 4 is a block diagram of a processing system 400 comprising a conventional plasma etching system 402 and a process monitoring system 404 coupled thereto in accordance with an embodiment of the present invention. As used herein, "coupled" means coupled directly or indirectly. The conventional plasma processing system 402 comprises a plasma chamber 406 coupled to a plasma processing system controller 408 via a recipe control port 410 and via a first control bus 412 or other suitable interface and a process monitoring system 404. The plasma chamber 406 comprises a viewport 414 for coupling electromagnetic emissions from the inside of the chamber 406 to the outside of the chamber. The emissions are primarily optical wavelengths within the range from about 180 to 1400 nanometers, generally represented as 416 in FIG. 4. The emissions are produced by plasma 418 sustained within the plasma chamber 406. The plasma electromagnetic emissions 416 comprise emissions from a large number of plasma species (e.g., process gasses, reaction products, etc.). Note that the viewport 414 is shown positioned on the side of the plasma chamber 406, but may be positioned at any other location (e.g., on the top or bottom of the chamber 406) if desired.

The process monitoring system 404 comprises a spectrometer 420 coupled to a processor 422 in communication with system controller 408 via interface 432. The spectrometer 420 is positioned to collect the electromagnetic emissions 416 from the plasma 418 and to provide intensity information regarding a plurality of plasma electromagnetic emission wavelengths to the processor 422. A lens 424 and/or a fiber optic cable 426 are disposed between the viewport 414 and the spectrometer 420 for improving collection of the electromagnetic emissions 416 by the spectrometer 420.

In operation, a user 428 (e.g., a person in charge of a wafer fabrication process) supplies (via a second control bus 430 or other suitable interface) the plasma processing system controller 408 with a set of instructions for generating the plasma 418 within the plasma chamber 406 (i.e., a plasma recipe). Alternatively, a remote computer system for running a fabrication process may supply the plasma processing system controller 408 with a plasma recipe (e.g., as supplied by the user 428 or as stored within a plasma recipe database). A typical plasma recipe includes processing parameters such as the pressure, temperature, power, gas types, gas flow rates and the like used to initiate and maintain the plasma 418 within the plasma chamber 406 during plasma processing. Once the plasma processing system controller 408 receives a plasma recipe from the user 428, from a remote computer system, from a manufacturing execution system, etc., the plasma recipe is supplied to the recipe control port 410 via the first control bus 412, and the recipe control port 410 (or the plasma processing system controller 408 itself if the recipe control port 410 is not present) establishes and maintains within the plasma chamber 406 the processing parameters specified by the plasma recipe.

During a plasma process within the plasma chamber 406, the plasma 418 generates electromagnetic emissions 416 having wavelengths primarily in the optical spectrum (e.g., from about 180 to 1400 nanometers), although both ultraviolet and infrared wavelengths also may result. A portion of these electromagnetic emissions (e.g., the electromagnetic emissions 416) travels through the viewport 414 and reach the inventive process monitoring system 404. Note that while the electromagnetic emissions 416 are represented generally by three emission wavelengths in FIG. 1, it will be understood that the electromagnetic emissions 416 typically comprise many more wavelengths.

The spectrometer 420 receives the electromagnetic emissions 416 via the lens 424 and the fiber optic cable 426. In response thereto, the spectrometer 420 spatially separates the electromagnetic emissions 416 based on wavelength (e.g., via a prism or a diffraction grating, and generates detection signals (e.g., detection currents) for a plurality of the spatially separated wavelengths. The processor 422 continually monitors the detection signals from the spectrometer 420 and provides feedback to the system controller 408 and/or the user 428 about the plasma state. The user 428 and/or system controller 408 can adjust the processing parameters to maintain the plasma 418 in a steady state.

Figure 5:
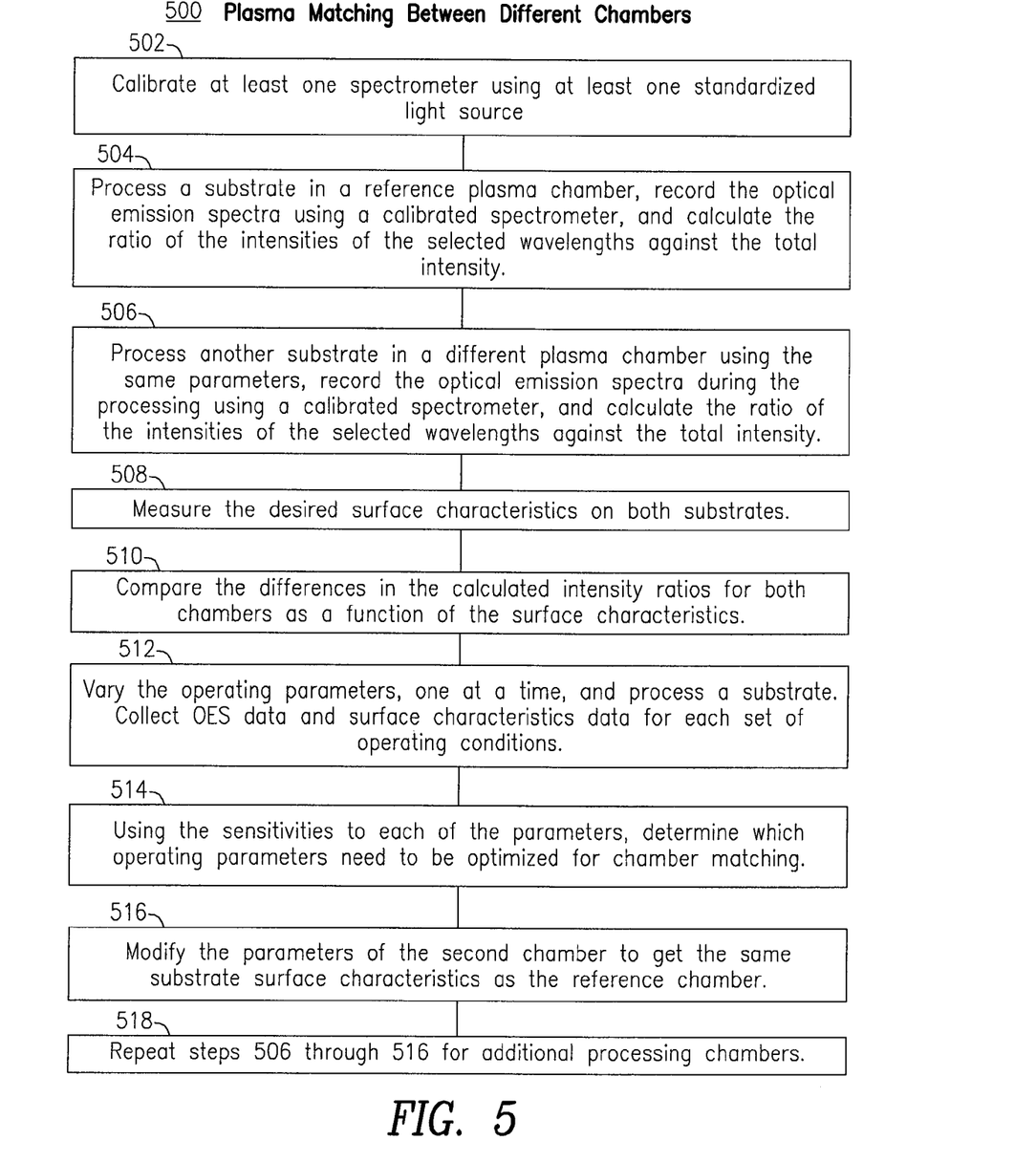
FIG. 5 is a flowchart illustrating steps of a method of plasma matching between two different processing chambers.

Another embodiment is illustrated in FIG. 5, which shows a method 500 of matching plasma states between different processing chambers. It should be understood that this flowchart does not require steps be performed sequentially but has been created as a convenient means of describing the invention. Step 502 involves the calibration of a spectrometer, as discussed above with respect to FIG. 1. In step 504, a reference plasma processing chamber is employed to process a substrate with the desired plasma recipe. The optical emission spectra of the plasma is monitored throughout the processing. The ratio of the intensities of the selected wavelengths to the total intensity is determined. These ratios are used as a marker of the characteristics of the reference process. A substrate is processed using a chamber other than the reference chamber in step 506. The same plasma recipe as that of 504 is employed with the second chamber and the OES is collected. The same characteristic wavelength ratios are determined as with the reference chamber processing. The surface characteristics of processed substrates from 504 and 506 are measured in 508. These characteristics include, but are not limited to, the degree of nitrogen dosing or oxygen dosing. The surface characteristics are typically measured by x-ray photoelectron spectroscopy, but other techniques can be used as appropriate. The wavelength ratios are correlated to the surface characteristics for the second substrates and compared to the correlation from the reference process in 510. The operating parameters of the processing chamber are modified in 512, one at a time, and a substrate is processed. The OES data and surface characteristics are measured for each modified operating condition. Using the correlated data from the modified conditions 512, the sensitivity to each parameter is determined 514. The appropriate parameter(s) are modified 516 on the second chamber to obtain the same surface characteristics as that of the reference chamber. The process can be repeated 518 for multiple chambers.

As a specific example of the process immediately described above, two external lights sources are provided to calibrate a spectrometer for a DPN process to measure nitridation of substrates. For the first light source, the total intensity (area under the curve is calculated, and for the second light source, the intensities of selected peaks, area under each peak and ratios of selected peaks are calculated for known light sources. The calibrated spectrometer is then used on a DPN chamber for two best known conditions: (1) 200 W, CW, 30 s, 20 MT, 5 SLM nitrogen and no chucking and (2) 1000 W, 5% duty cycle, 20 mT, 30 s and 5 SLM of nitrogen. It will of course be recognized, that these two conditions are exemplary only. Spectra for the two conditions are collected and the area under key species peaks are expressed as a fraction of (i) peak close to wavelength in reference for the second source and also as a total fraction of the total area for the first source.

The same procedure is then repeated on another DPN chamber with the same recipe conditions, and the same spectra are collected and the area under key species are expressed the same way as in the reference chamber. The differences between the two chambers in calculated values using the spectra and XPS N-dos data are determined, and differences (if any) between the two chambers are correlated. Then, parameters for the second chamber are varied on at a time, for example, power, pressure, reflected power, nitrogen flow, He leak amount, moisture content variation, etc. Differences between in calculated values using the spectra and XPS N-does are determined, and sensitivities are correlated. Using the sensitivities to each of the parameters, a method for chamber matching can be implemented. For example, if two chambers differ by 5% in XPS N-dose, the power, pressure or other parameter can be adjusted by a certain amount. The actual adjustment must be based on data from each tool/chamber. If the forward power from each chamber in the process step is different, then the powers must be adjusted. If the reflected power in one chamber is high, the recipe can be tuned to lower the reflected power. If the powers are determined to be the same, another parameter, for example, pressure, He leak, etc. can be investigated until the source of difference is corrected and the second chamber matches the reference chamber. This concept can be extended to additional chambers so that chambers can all be matched to a reference chamber. If the chambers are still not matched with XPS N-dose, even after allowing a defined offsets in power are allowed using the RF Calibration Tables, then parameters outside DPN chamber can be investigated such as leaks in a rapid thermal processing (RTP) chamber step prior to DPN or wafer temperature coming out of RTP chamber, or leaks in PNA chamber or metrology queue time. Eventually, the source of process discontinuity can be identified until the second and subsequent processes are calibrated to the substrates produced according to the reference process.

Figure 6:
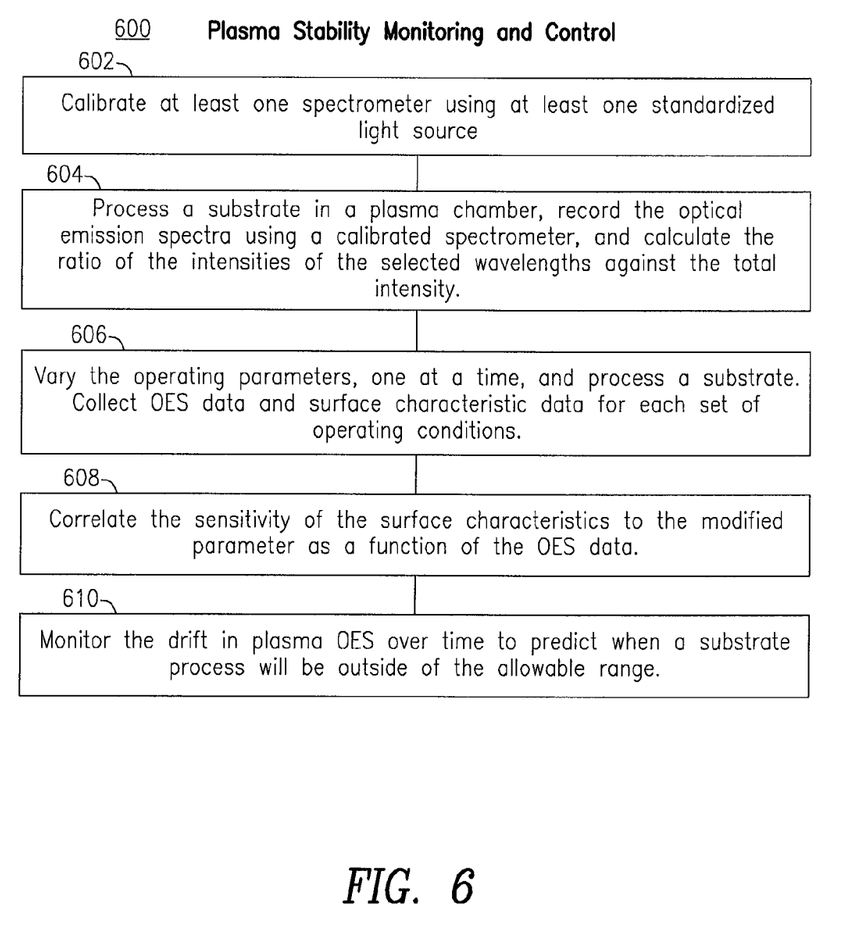
FIG. 6 is a flowchart illustrating steps of a method of plasma stability monitoring for a single processing chamber.

A further embodiment is illustrated in FIG. 6, which shows the flowchart for 600 a method of monitoring the plasma stability within a chamber. A spectrometer calibrated with a standardized light source 602 is required. See 100 for further details as to the spectrometer calibration. A substrate is processed 604 using the plasma chamber that will be monitored. The OES data is recorded using the calibrated spectrometer, and the surface characteristics of the substrate are measured. The operating parameters of the plasma chamber 606 are varied and a substrate is processed while monitoring the OES. The surface characteristics are measured for each substrate processed. The sensitivity of the surface characteristic to the plasma OES can be correlated 608 from the modified processing parameters. The plasma process OES is monitored 610 to predict when a process will result in an unacceptable product. By monitoring the OES data on a continuous basis, the user will be able to ensure that preventative maintenance can be performed, and reduce the number of unacceptable substrate processing events.

Techniques for matching a newly manufactured or newly maintained plasma chamber to an absolute reference are desired in the semiconductor processing field. Additionally, methods to effectuate the comprehensive calibration of a new or recently maintained plasma chamber are needed for improved process repeatability and control.

In a production environment, if a substrate process chamber shows signs of process drifting, or otherwise operating in a faulty manner, the wafer processing would need to be immediately stopped to ensure that incorrect processing does not affect many wafers. The source of the chamber fault would need to be quickly diagnosed such that cause(s) of the fault can be repaired and the chamber restarted. For example, if the source of chamber fault is low source power, traditional diagnosis would require a technical expert to review the data log and then propose possible causes. Such a procedure would take from a few hours to a couple of days to identify the problem source. Using the principles according to embodiments of the present invention, a series of diagnostic perturbation runs will enable the user to determine what changes have occurred to the processing system. The OES signals and surface characteristics generated from these diagnostic runs can be compared against the OES and surface characteristic data generated in a reference chamber as a means of chamber matching. Thus, the methods according to embodiments of the invention also can be used to monitor stability of the same chamber over three or more months. For example, if nitrogen dose (N-dose) is being monitored, by collecting the N-dose drift data, spectral drift data and electrical device drift data, it is possible to calculate the sensitivity of device parameters and N-dose to spectral parameter variation over time. It is also possible to prescribe when the chamber drifts close to getting out of the allowable range in the future, process maintenance can be performed to bring the chamber back into an acceptable operating state. Also, during the monitoring period, the stability of plasma can be characterized.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

We claim:

1. A method of matching the performance of process chambers, comprising:

calibrating at least a first spectrometer with at least a first standardized light source and collecting calibration data;

collecting optical emission spectroscopy (OES) data using the at least first spectrometer during a first reference process utilizing a reference substrate, under known process parameters;

collecting OES data using the at least first spectrometer during a second plasma process for a second substrate under process parameters substantially the same as the first process; and measuring the degree of surface characteristic modification for the first and second substrates and correlating the degree of surface characteristic modification with the OES data for each substrate, wherein the correlation of OES data and surface characteristic modification of the second process is compared to the correlation of OES data and surface characteristic modification of the first process.

2. The method of claim 1 further comprising:

varying the process parameters of the second process, and processing a substrate using the varied parameters while collecting OES data;

measuring the degree of surface characteristic modification of the substrate using varied parameters;

correlating the degree of surface characteristic modification and the OES data obtained from the substrate using varied process to determine the OES data sensitivity to the varied process parameters; and adjusting the process parameters of the second process based on the correlation data so that the surface characteristic modification of at least a third processed substrate would match the reference substrate.

3. The method of claim 2 wherein the second process is performed in the same chamber operated at a later time.

4. The method of claim 2 wherein the modified process parameter of the second process is selected from a group consisting of RF power, chamber pressure, reflected power, nitrogen flow rate, helium leak amount, wafer type, wafer temperature, base oxide amount, helium content of the nitrogen, oxygen content and moisture content.

5. The method of claim 1 wherein the first spectrometer is calibrated by measuring total intensity of light generated by the first standardized light source at selected wavelengths.

6. The method of claim 5, wherein the first spectrometer is calibrated using a second standardized light source and measuring the intensity of light at selected wavelengths.

7. The method of claim 6 wherein the second standardized light source emits discrete wavelengths.

8. The method of claim 6 wherein the standardized light sources are comprised of a plurality of light emitting diodes.

9. The method of claim 6 wherein the standardized light sources are located inside the process chamber.

10. The method of claim 6 wherein the standardized light sources are located outside of the process chamber.

11. The method of claim 5 wherein the second process is performed in the same chamber operated at a later time.

12. The method of claim 5 wherein the first standardized light source has a continuous spectral emission.

13. The method of claim 1 wherein the process is selected from a group consisting of decoupled plasma nitridation, decoupled plasma oxidation, atomic layer deposition, plasma immersion ion implantation, plasma enhanced atomic layer deposition, remote plasma oxidation, and argon sputtering.

14. A method of monitoring the plasma stability of a processing chamber, comprising:
  calibrating at least a first spectrometer with at least a first standardized light source and collecting calibration data;
  collecting optical emission spectroscopy (OES) data using the at least first spectrometer during a reference plasma process for a reference substrate in a processing chamber under known process parameters;
  collecting OES data using the at least first spectrometer during a second plasma process for a second substrate in the same processing chamber under process parameters substantially the same as the first process and comparing the OES data obtained during the second process to the calibration data;
  varying the processing parameters of the process, and processing a substrate under the varied parameters while collecting OES data;
  measuring the degree of modification of a surface characteristic of the processed substrates and correlating the degree of modification of a surface characteristic and the OES data to determine the sensitivity to the modified process parameters; and
  monitoring the OES data during processing on at least a second substrate to predict when the at least second substrate will have a surface characteristic outside of the acceptable range.

15. The method of claim 14 wherein only one spectrometer is employed.

16. The method of claim 14 wherein the modified processing parameter of the process is selected from a group consisting of RF power, chamber pressure, reflected power, nitrogen flow rate, helium leak amount, wafer type, wafer temperature, base oxide amount, helium content of the nitrogen, oxygen content and moisture content.

17. The method of claim 14 wherein the first spectrometer is calibrated by measuring total intensity of light generated by the first standardized light source at selected wavelengths.

18. The method of claim 14 wherein the first spectrometer is calibrated using a second standardized light source and measuring the intensity of light at selected wavelengths.

19. The method of claim 18 wherein the standardized light sources comprises a plurality of light emitting diodes.

20. The method of claim 18 wherein the standardized light sources are located inside the processing chamber.

21. The method of claim 18 wherein the standardized light sources are located outside of the processing chamber.

22. The method of claim 14 wherein the process is selected from a group consisting of decoupled plasma nitridation, decoupled plasma oxidation, atomic layer deposition, plasma immersion ion implantation (P3i), plasma enhanced atomic layer deposition (PE ALD), and remote plasma oxidation (RPO).

* * * * *